United States Patent [19]

Millick, III

[11] 4,076,946

[45] Feb. 28, 1978

[54] HYDROGENATION OF MOLTEN ALDEHYDIC DIMETHYL TEREPHTHALATE

[75] Inventor: William H. Millick, III, New Castle, Del.

[73] Assignee: Hercofina, Wilmington, Del.

[21] Appl. No.: 430,102

[22] Filed: Jan. 2, 1974

[51] Int. Cl.² ............... C07C 67/48; C07C 69/82
[52] U.S. Cl. .................................................. 560/78
[58] Field of Search ................ 260/475 B, 475 PR

[56] References Cited

U.S. PATENT DOCUMENTS

| | | | |
|---|---|---|---|
| 3,666,791 | 5/1972 | Chikawa et al. | 260/475 PR |
| 3,803,003 | 4/1974 | Matsuzawa et al. | 260/475 PR |
| 3,803,212 | 4/1974 | Winnick et al. | 260/475 PR |

FOREIGN PATENT DOCUMENTS

| | | | |
|---|---|---|---|
| 164,012 | 7/1953 | Australia | 260/475 B |
| 744,412 | 2/1956 | United Kingdom | 260/475 B |
| 955,516 | 4/1964 | United Kingdom | 260/475 B |

OTHER PUBLICATIONS

Groggins, Unit Processes in Organic Synthesis, 5th Ed., pp. 599,600 and 608-611 (1952).

*Primary Examiner*—Jane S. Myers
*Attorney, Agent, or Firm*—George H. Hopkins

[57] ABSTRACT

Disclosed is a process for the catalytic hydrogenation of the aldehyde content of molten aldehydic dimethyl terephthalate (DMT). The process comprises first dissolving in the molten aldehydic DMT a quantity of molecular hydrogen sufficient to hydrogenate at least a substantial portion of the aldehydic content, and then contacting the molten aldehydic DMT with its dissolved hydrogen content with a hydrogenation catalyst for a period of time sufficient for reaction of the dissolved hydrogen with the aldehydic content to take place, but insufficient for substantial ring hydrogenation to occur.

5 Claims, 1 Drawing Figure

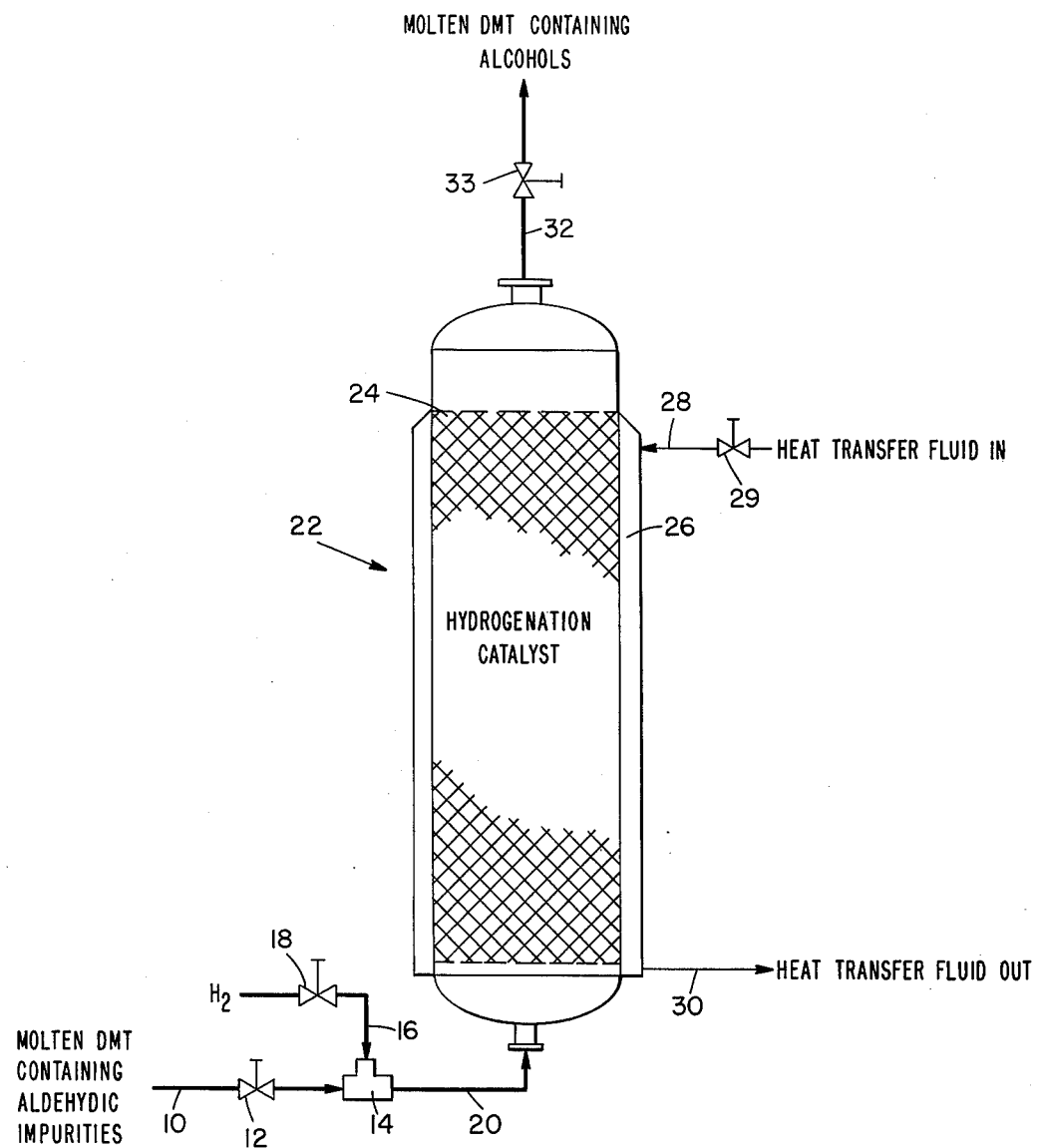

HYDROGENATION OF MOLTEN ALDEHYDIC DIMETHYL TEREPHTHALATE

This invention is in the chemical arts. It relates to dimethyl terephthalate (DMT).

DMT is one of the principal chemicals from which the now very common polyethylene terephthalate fiber is made. To obtain polyethylene terephthalate fiber of high quality, highly stringent quality specifications have been imposed on DMT. In one such specification for a fiber grade DMT the maximum permitted content of aldehyde-ester (4-carbomethoxybenzaldehyde) and other aldehydes is only 20 p.p.m. (parts by weight per million parts by weight of DMT).

One process for the production of DMT comprises oxidizing p-xylene in the liquid phase with molecular oxygen to form p-toluic acid, esterifying the acid with methanol to form methyl p-toluate, oxidizing the methyl p-toluate with molecular oxygen to monomethyl terephthalate, and esterifying the monomethyl terephthalate with methanol to form DMT. As commercially practiced at the present time, the process is continuous with the oxidation steps being carried out together in the same reactor or reactors (oxidation stage) and the esterification steps being performed together in a separate reactor or in separate reactors (esterification stage). The reaction mixture from the esterification stage comprises DMT, intermediate oxidation products and by-products. These intermediate oxidation products and by-products include aldehyde-ester and other aldehydic impurities. In treating the reaction mixture to isolate DMT, a methyl p-toluate fraction is separated by distillation and sent to the oxidation stage, and then a crude DMT fraction is separated by distillation. To minimize aldehydic impurities in the crude DMT fraction, an effort is made to remove these impurities in the methyl p-toluate fraction. However, the boiling points of all these aldehydic impurities are very close to that of DMT. Consequently, there is a significant concentration of DMT in the methyl p-toluate fraction and, therefore, recycle of significant amounts of DMT through the oxidation stage, which reduces substantially the DMT production rate. Moreover, there is still such a high concentration of aldehydic impurities in the crude DMT fraction, concentrations of the order of 5000-10,000 p.p.m. being not uncommon, it is necessary to reduce the aldehydic content to at least the desired level. Heretofore in connection with the above-described process, this has been done by a series of crystallization steps.

However, British Patent Specification No. 955,516 discloses a process in which DMT containing aldehydic impurities is subjected to catalytic hydrogenation to reduce the aldehydic impurities to compounds which either can be tolerated in fiber grade polyethylene terephthalate, or can be more easily separated from DMT. While that patent specification in its generic disclosures does not disclose the details of the process other than that the hydrogenation catalyst must be selective (that is, one that promotes hydrogenation of the formyl group or aldehyde moiety, but not aromatic rings or the carbomethoxy group), and that copper-chromium oxide or Raney copper meets this requirement, the working examples of the patent specification indicate a process based on conventional laboratory procedure. In such process the hydrogenation catalyst and a quantity of aldehydic DMT are charged to an autoclave of the rocking or shaker type, or of the stirrer type. Then molecular hydrogen is introduced into the autoclave and established at an initial hydrogen pressure as low as 10 kg./sq. cm. to as high as 125 kg./sq. cm. The autoclave contents are established at a temperature as low as 150° C. to as high as 250° C. and maintained at this temperature for 2-3 hours. The resulting reaction mixture is then cooled and removed from the autoclave. While these conditions may result in substantial reduction of aldehydic impurities without subsequent aromatic ring reduction (because of the particular catalyst disclosed in the British patent specification), there is experimental evidence that the rate of hydrogenation of the aldehyde moiety under the conditions is slow and that the catalyst loses activity too quickly to be commercially practical. When using other hydrogenation catalysts under otherwise the same conditions, the result can be significant ring hydrogenation and consequent appearance of dimethyl hexahydroterephthalate which is to be avoided.

It has been found that, when molten aldehydic DMT is subjected to catalytic hydrogenation with a catalyst that tends to promote aromatic ring hydrogenation at the temperature of molten DMT, hydrogenation of the aldehydic content tends to take place at a faster rate than aromatic ring hydrogenation. It further has been found that, when palladium is the catalyst and the aldehydic impurities are at a concentration above a certain concentration (herein called threshold concentration), which is dependent on the mode of catalyst contact, hydrogen availability, and the like, hydrogenation of the aldehydic content proceeds without significant ring hydrogenation until the aldehydic content concentration falls below that concentration.

It appears, therefore, that the amount of time which the molten aldehydic DMT, the molecular hydrogen and the catalyst are in contact must be controlled if substantial ring hydrogenation is to be avoided when the catalyst tends to promote ring hydrogenation at the prevailing temperature.

The amount of time of such contact is difficult to control, however, in the procedure of British Patent Specification 955,516. It also is difficult to control in hydrogenation reactors involving a catalyst bed in which the material to be hydrogenated is passed either in molten condition or in solution in an inert solvent through the bed while molecular hydrogen is passed either countercurrently or cocurrently through the bed. This is true regardless of whether the bed is operated in an unflooded or flooded condition.

The reason for this difficulty appears to be the inefficient random nature of the contact between the material to be hydrogenated, the molecular hydrogen, and the catalyst.

Hence, the problem to which this invention provides a solution is to provide a more efficient uniform contact between the material to be hydrogenated, the molecular hydrogen, and the catalyst.

In summary, this invention, considered broadly, provides a process for catalytically hydrogenating hydrogenatable material in the liquid phase (molten or in solution in an inert liquid solvent) with molecular hydrogen. According to the inventive process, molecular hydrogen is first dissolved in the liquid phase, and the resulting solution then is contacted with the hydrogenation catalyst for the amount of time selected to give the desired extent of hydrogenation.

In one embodiment of the process molten aldehydic DMT is hydrogenated. In this embodiment a quantity of molecular hydrogen sufficient to hydrogenate at least a substantial portion of the aldehydic content of the molten aldehydic DMT is dissolved therein, and the resulting mixture is contacted with said catalyst for a period of time sufficient for a substantial proportion of the aldehydic content of the DMT to be hydrogenated with minimal ring hydrogenation.

DMT melts at 140.65° C. Accordingly, in the process of this invention the temperature of the aldehydic DMT is established and maintained at about 141°–240° C. Higher temperatures are not recommended because of the danger of pyrolysis of the DMT.

The quantity of molecular hydrogen admixed with the molten aldehydic DMT is dependent on the concentration of the aldehydic impurities, in the case of palladium as the catalyst the threshold concentration, the dimethyl hexahydroterephthalate content of the reaction mixture resulting from the catalyst contacting step, and the way in which the catalyst contacting is carried out (batch process or continuous process, upflow fixed catalyst bed reactor or downflow fixed catalyst bed reactor, etc.). No generalization can be made other than the quantity of hydrogen should be such that when the mixture is contacted with the catalyst there will be enough available to hydrogenate a substantial proportion of the aldehydic impurities to the selected extent. In this connection, except when palladium is the catalyst and the aldehydic content is above the threshold concentration, increasing the quantity of molecular hydrogen in the solution of DMT and hydrogen enhances the rate of formation of dimethyl hexahydroterephthalate. In a preferred practice of the DMT embodiment of the process of this invention, which is continuous, a recommended quantity of molecular hydrogen admixed with the DMT when it is at 155° C. and contains, for example, 500 p.p.m. of aldehyde-ester, which in most instances involving palladium as the catalyst is above the threshold concentration, is that which is equivalent to the amount of molecular hydrogen in solution in molten DMT at a hydrogen pressure of 3.5 kilograms per square centimeter guage at 155° C.

The hydrogenation catalyst employed in the second step of the DMT embodiment of the process of this invention can be any catalyst for hydrogenating aldehydes. Representative of such a catalyst are palladium, nickel (including Raney nickel), ruthenium, rhodium, platinum, cobalt, iron, molybdenum, silver, palladium chloride, nickel oxide, cobalt nitrate, copper-chromium oxide, Raney copper, and the like. Preferred are palladium and nickel. The catalyst can be supported or unsupported.

In the DMT embodiment the period of time in which the catalyst is in contact with the mixture of molecular hydrogen and molten aldehydic DMT is selected as above stated. It should be insufficient for substantial ring hydrogenation. While the selection depends to a certain extent on what is desired, in a preferred practice in which palladium is the hydrogenation catalyst and the aldehyde content of DMT is substantially above the threshold concentration, the period of time is selected so that hydrogenation of the aldehydic impurities does not reduce the concentration of the aldehyde moiety below the threshold concentration.

As already indicated above, the admixing and contacting steps of this invention can be carried out by various ways and means.

In one batch practice of the DMT embodiment, the hydrogenation catalyst and molten aldehydic DMT with dissolved molecular hydrogen are introduced into an autoclave. The autoclave contents are agitated or stirred at 141°–240° C. for a period of time sufficient to substantially hydrogenate the aldehydic impurities, but insufficient to substantially ring hydrogenate. At the end of this period of time the autoclave is opened and the resulting reaction mixture is separated from the hydrogenation catalyst.

In the continuous practice of the DMT embodiment of the process of this invention, molecular hydrogen is dissolved in the molten aldehydic DMT, and the resulting solution is passed through a bed of hydrogenation catalyst. The distance of travel of the solution through the bed and the rate of flow of solution through the bed are selected so that at least a substantial portion of the aldehydic impurities are hydrogenated without substantial ring hydrogenation. In one practice the catalyst bed is established and maintained in a downflow reactor. In another practice the catalyst bed is established and maintained in an upflow reactor.

The initial aldehyde concentration in the molten aldehydic DMT to be treated according to this invention can be high enough that the amount of molecular hydrogen initially present or the amount of contact between the catalyst, molecular hydrogen and catalyst is not enough to hydrogenate the desired proportion or substantially all of the aldehydic impurities. In such event, the process steps are again repeated until the aldehyde concentration has been reduced at least to the desired level. In the continuous process practice of the DMT embodiment repeating the process steps can be accomplished in a number of ways. In one practice a portion of the reaction mixture resulting from the catalyst contact step is recirculated through the two steps while the remainder of the reaction mixture is removed as product. In another practice the reaction mixture from the catalyst contact step is introduced into another stage in which molecular hydrogen is dissolved in the reaction mixture and the resulting solution then is passed into contact with hydrogenation catalyst for the period of time called for under the concepts of this invention.

The best mode now contemplated of carrying out the invention is illustrated by the drawing which forms a material part of these disclosures, and which depicts diagrammatically a preferred specific continuous practice of the DMT embodiment of the process of this invention. This invention is not limited to this embodiment.

In the specific process illustrated by the drawing, molten DMT containing aldehydic impurities is conducted by way of a feed conduit 10 equipped with a flow rate control and shutoff valve 12 into an infeed leg of a mixing tee 14. Gaseous molecular hydrogen is introduced by way of a hydrogen supply conduit 16 fitted with a flow rate control and shutoff valve 18 into a second infeed leg of the mixing tee 14. Inside the mixing tee 14 the molecular hydrogen is admixed with the molten DMT and its content of aldehydic impurities, thereby dissolved in the molten aldehydic DMT. The resulting solution is transferred from the output leg of the mixing tee 14 through the transfer conduit 20 to the inlet of the catalyst contact reactor 22.

The catalyst contact reactor 22 is of the upflow type. Within its interior is a bed 24 of particles of hydrogenation catalyst. The reactor comprises a surrounding jacket 26 with an inlet in the region of the bottom end thereof in communication with a heat transfer fluid feed conduit 28 equipped with a flow rate control and shut-off valve 29 and with an outlet in the region of the top end thereof in communication with a heat transfer fluid discharge conduit 30. When desired, under normal operative conditions a heat transfer fluid such as, for example, steam, is introduced into the jacket by way of the feed conduit 28, and spent heat transfer fluid is withdrawn from the jacket 26 by way of the discharge conduit 30. By adjustment of the valve 29, the flow rate of heat transfer fluid through the jacket 26 and thus the temperature of the contents of the catalyst contacting reactor is controlled.

The solution of molten aldehydic DMT and molecular hydrogen introduced into the inlet at the bottom of the catalyst contact reactor 22 passes upwardly through the hydrogenation catalyst bed 24. Reaction between the dissolved molecular hydrogen and aldehydic impurities is thereby promoted, resulting in the formation of alcohols and reduction in the concentration of aldehydic impurities. The resulting reaction mixture reaching the top of the catalyst contact reactor 22 is withdrawn therefrom by way of discharge conduit 32 which is equipped with a flow rate control and shut-off valve 33.

The height of the catalyst bed 24 and the flow rate of the solution of molecular hydrogen and impure molten DMT through the catalyst bed 24 are selected to give a residence time of the solution in the catalyst bed 24 sufficient for hydrogenation of a substantial portion of the aldehydic impurities with minimal or no ring hydrogenation. The rate of flow of solution through the catalyst bed 24 is regulated by means of the discharge conduit valve 33, the impure molten DMT feed conduit valve 12 or both of these valves.

Preferably, periodically the reaction mixture discharged from the catalyst contact reactor 22 by way of conduit 32 is analyzed for aldehyde ester content or aldehydic impurities content and for dimethyl hexahydroterephthalate content. On the basis of these periodic analyses, the rate of introduction of molecular hydrogen to the mixing tee 14 (the hydrogen pressure at the tee 14) the rate of flow of impure molten DMT through the mixing tee 14, or both, and the rate of discharge from the reactor of reaction mixture are adjusted by the respective valves to minimize the aldehyde-ester or aldehydic impurities content and the dimethyl hexahydroterephthalic content.

In an especially preferred practice of the DMT embodiment of the process depicted in the drawing, palladium is employed as the hydrogenation catalyst, and the aldehydic content of the molten aldehydic DMT is substantially above the threshold concentration. In this embodiment the infeed rate of the molten aldehydic DMT, the molecular hydrogen flow rate of hydrogen pressure at the tee 14, and rate of discharge of reaction mixture from the reactor 22 are established and maintained so that hydrogenation of the aldehydic impurity reduces the aldehydic impurity concentration to, but not beyond the threshold concentration. In this connection in the laboratory in an upflow reactor in which the catalyst was 0.5% by weight palladium on carbon, the molecular hydrogen was dissolved as in the process of the drawing at 1-9 kg./sq. cm. and the aldehyde-ester threshold concentration at 155° C. was about 150 p.p.m. On the other hand, in a laboratory co-current downflow system in which the flow of molten aldehydic DMT and molecular hydrogen gas was downwardly together through a catalyst bed of 1% by weight palladium on carbon at 155° C. and hydrogen pressure of 0.2-4 kg./sq. cm. the threshold concentration was about 350 p.p.m. Hence, bearing in mind the extremely low aldehyde-ester requirement for at least one fiber grade DMT, this especially preferred practice of the DMT embodiment of the process depicted in the drawing is intended for that part of the purification section of the DMT production plant having a stream of molten aldehydic DMT with an aldehyde-ester content of 200-2000 p.p.m., which is followed by one or more purification steps such as distillation, crystallization and the like.

Hydrogenation of the aldehydic impurities converts them to alcohols which in a number of instances can be tolerated in the production of fiber grade polyethylene terephthalate. For DMT destined for such instances, the molten reaction mixture discharged from the catalyst contact reactor 22 when it is the last DMT treatment step in a DMT production plant can be conveyed directly to storage or to the polyethylene terephthalate polymer producing plant, or solidified, formed into divided particles and stored or packaged. In those other instances in which alcoholic impurities and even trace concentrations of dimethyl hexahydroterephthalate are not wanted, the molten reaction mixture discharged from the catalyst contact reactor 22 is conveyed to a separation station and treated to separate therefrom the alcoholic content as well as dimethyl hexahydroterephthalate. An example of such a separation treatment is distillation. The alcohols and dimethyl hexahydroterephthalate generally have boiling points substantially different from that of DMT. Thus, the boiling point of the alcohol corresponding to the aldehyde ester is higher than that of DMT, while the boiling point of dimethyl hexahydroterephthalate is lower than that of DMT. Consequently, DMT, free of these alcohols and dimethyl hexahydroterephthalate, can be isolated by distillation from the reaction mixture discharged from the catalyst contact reactor 22.

The following are typical conditions for the practice of the process depicted in the drawing, "$v$" being volume, "$w$" being weight, p.p.m. being $w$ per million $w$ of DMT, and "$m$" being a unit of linear measure, the relationship of $v$ to $w$ to $m$ being as the liter to the kilogram to the centimeter.

| | |
|---|---|
| Aldehyde ester concentration of DMT in conduit 10 | = 530 p.p.m. |
| Flow rate of molten DMT containing aldehydic impurities through conduit 10 | = 0.80 v/hr. |
| Hydrogen pressure at mixing tee 14 | = 1.9 kg./sq. cm. |
| Catalyst | = 0.5% Palladium on carbon |
| Diameter of catalyst bed | = 2.5 m |
| Height of catalyst bed | = 27 m |
| Temperature of catalyst contact reactor 22 contents | = 155° C. |
| Aldehyde ester content of reaction mixture in conduit 32 | = 100 p.p.m. |
| Dimethyl hexahydroterephthalate content of reaction mixture in conduit 32 | = <20 p.p.m. |

Thus, this invention provides more efficient ways and means for catalytically hydrogenating hydrogenatable material in the liquid phase, and particularly for catalytically hydrogenating the aldehydic content of molten aldehydic DMT with minimal ring hydrogenation.

Other features, advantages and specific embodiments of this invention will become readily apparent to those exercising ordinary skill in the art after reading the foregoing disclosures. Such specific embodiments are within the scope of the claimed subject matter unless expressly indicated to the contrary by claim language. Moreover, while a specific embodiment of this invention has been described in considerable detail, variations and modifications of it can be effected without departing from the spirit and scope of the invention as disclosed and claimed.

I claim:

1. In a process for treating molten aldehydic DMT by subjecting it to catalytic hydrogenation with a catalyst that not only promotes hydrogenation of the aldehydic content, but also tends at the temperature of the molten DMT to promote ring hydrogenation, the improvement for minimizing said ring hydrogenation, which comprises dissolving in said molten aldehydic DMT a quantity of molecular hydrogen sufficient to hydrogenate at least a substantial portion of said aldehydic content without substantially enhancing the rate of formation of dimethyl hexahydroterephthalate, and contacting the resulting solution with a catalytic quantity of said catalyst for a period of time sufficient for the molecular hydrogen to hydrogenate at least a substantial portion of the aldehydic content with minimal ring hydrogenation.

2. A process according to claim 1 in which said solution of molten aldehydic DMT and molecular hydrogen is passed through a bed of particles of said catalyst, the length of travel through said bed and the rate of flow through said bed being selected to provide said period of time.

3. A process according to claim 2 in which the temperature at which said solution is contacted with said catalyst is about 141°–240° C., and said catalyst is selected from the group consisting of palladium and nickel.

4. A process according to claim 3 in which said catalyst is palladium, the initial concentration of said aldehydic content is substantially above the threshold level, said quantity of molecular hydrogen is sufficient for the reduction of the concentration of said aldehydic content to a selected concentration, said threshold concentration being the limit, and said period of time is sufficient for the concentration of said aldehydic content to be reduced by hydrogenation of said selected concentration.

5. A process according to claim 4 in which the initial concentration of aldehyde ester in said molten aldehydic DMT is 200–2000 p.p.m.

* * * * *

UNITED STATES PATENT AND TRADEMARK OFFICE
CERTIFICATE OF CORRECTION

PATENT NO. : 4,076,946
DATED : February 28, 1978
INVENTOR(S) : William H. Millick III It is certified that error appears in the above-identified patent and that said Letters Patent are hereby corrected as shown below:

Col. 3, Line 28,
  Insert the following after "extent":
    "without enhancing the rate of formation of dimethyl hexahydroterephthalate"

Col. 5, Line 55,
  "of" -- should read -- "or"

Signed and Sealed this

Eighteenth Day of July 1978

[SEAL]

Attest:

RUTH C. MASON
*Attesting Officer*

DONALD W. BANNER
*Commissioner of Patents and Trademarks*